United States Patent [19]
Yamamoto et al.

[11] Patent Number: 5,383,050
[45] Date of Patent: Jan. 17, 1995

[54] ORGANIC NONLINEAR OPTICAL MATERIAL

[75] Inventors: Hironobu Yamamoto, Yokohama, Japan; Robert Johnson, Hoboken, N.J.; Satoru Funato, Kawagoe, Japan

[73] Assignee: Hoechst Aktiengesellschaft, Frankfurt am Main, Germany

[21] Appl. No.: 132,040

[22] Filed: Oct. 5, 1993

[30] Foreign Application Priority Data

Oct. 7, 1992 [JP] Japan .................................. 4-268283

[51] Int. Cl.⁶ .............................................. G02F 1/35
[52] U.S. Cl. .................................. 359/326; 252/582; 252/589; 385/122
[58] Field of Search ............... 252/582, 583, 587, 588, 252/589; 359/326–332; 385/122; 372/21–22

[56] References Cited

U.S. PATENT DOCUMENTS

| | | | |
|---|---|---|---|
| 4,131,463 | 12/1978 | Tusboi et al. | 430/31 |
| 5,041,516 | 8/1991 | Fréchet et al. | 528/44 |
| 5,208,299 | 5/1993 | Bales et al. | 525/437 |

*Primary Examiner*—John D. Lee
*Attorney, Agent, or Firm*—Curtis, Morris & Safford

[57] ABSTRACT

The compounds 4-chloro-4'-hydroxybenzophenone, methyl 3,4-diaminobenzoate, N-(4-aminobenzenesulfonyl)-acetamide, methyl 4-hydroxy-3,5-dimethoxybenzoate, 2-chloro-4-cyano-6-methylaniline, 4'-hydroxy-2-phenylacetophenone and methyl 3,4-dihydroxybenzoate form high quality crystals with high melting point. They are useful for second order non-linear optical process devices such as wavelength conversion devices.

3 Claims, No Drawings

ORGANIC NONLINEAR OPTICAL MATERIAL

BACKGROUND OF THE INVENTION

This invention relates to nonlinear optical materials useful for wavelength conversion or parametric amplification of laser light in the fields of optical communication and optical information processing.

Nonlinear optical materials are today drawing the increasing attention of researchers in the field of optoelectronics. Nonlinear optical materials are those materials which interact with light to produce a nonlinear response. Second order nonlinear optical effects are exemplified by second harmonic generation (SHG) and the first-order electrooptic (EO) effect (Pockel's effect). These effects can be utilized to various ends such as halving the wavelength of laser light, electrooptic modulation and optical switching. Ongoing efforts, therefore, are being made to study nonlinear optical devices exhibiting these effects.

Nonlinear optical materials conventionally known to exhibit the SHG effect are inorganic materials such as lithium niobate ($LiNbO_3$) and potassium titanate phosphate (KTP) and the studies heretofore made on wavelength conversion devices utilizing the SHG have also focused on these inorganic materials. In recent years, however, organic nonlinear optical materials having a $\pi$-electron conjugated system have drawn the increasing attention because of their large optical nonlinearity and fast optical response, and many studies are being conducted in a search for promising materials.

Conventionally known organic nonlinear optical materials include urea, 2-methyl-4-nitroaniline (MNA), m-nitroaniline, N,N-dimethyl-2-acetylamino-4-nitroaniline (DAN), 3-methyl-4-nitropyridine-N-oxide (POM) and N-(4-nitrophenyl)-(L)-prolinol (NPP). Details about organic nonlinear optical materials may be found in, for example, (1) "Nonlinear Optical Properties of Organic and Polymeric Materials", ACS Symposium Series, 233 (1983), David J. Williams;

(2) "Nonlinear Optical Properties of Organic Molecules and Crystals", Vols. 1 and 2, Academic Press (1987), D. S. Chemla and J. Zyss;

(3) "Yuki Hisenkei Kogaku Zairyo (Organic Nonlinear Optical Materials)", Masao Karo and Hachiro Nakanishi, CMC Press (1985); and (4) "Shin-Yuki Hisenkei Kogaku Zairyo (Advanced Non-linear Optical Organic Materials)" Vols. I and II, T. Kobayashi, M. Umegaki, H. Nakanishi and N. Nakamura, CMC Press (1991).

The nonlinearity of organic compounds having a $\pi$-electron conjugated system is caused by the nonlinear polarization that occurs due to the interaction between laser light which comprises a strong electromagnetic wave and the delocalized $\pi$-electrons in the organic molecule of interest. In order to increase the magnitude of this nonlinear polarization or the second-order hiper polarizability $\beta$ of the molecule, an electron donating group (donor) or an electron withdrawing group (acceptor) is introduced into the $\pi$-electron conjugated system as a common technique for molecular design.

An issue with the organic compound synthesized by this molecular designing technique is the increment of its dipole moment due to the intramolecular charge transfer interaction. Hence, out owing to the dipole-dipole interaction, this organic compound tends to be centrosymmetric structure in the molecular cohesive process or crystallization, in which the dipole moments of adjacent molecules cancel out each other. In this case, none of second-order nonlinear optical effects such as SHG will be observed. It is almost impossible to predict the crystalline structure of a certain compound from its molecular structure even with the aid of a supercomputer. Therefore, in order to produce crystals having no centrosymmetric structure, empirical techniques are currently being employed, as exemplified by introducing an optically active group (chirality) or hydrogen pond into the $\pi$-electron conjugated system or reducing the dipole moment of the molecule in the ground state so as to attenuate the dipole-dipole interaction.

It should also be mentioned that compounds that experience a substantial charge transfer between donor and acceptor will shift the absorption maxima into longer wavelength, sometimes even to the visible region. Take, for example, the case of a wavelength conversion device with a semiconductor laser operating at 780–840 nm, the device will experience material deterioration or its conversion efficiency will decrease if the compound of which the device is made has absorption at the SHG range of 390–420 nm. Therefore, it is preferred for the crystals of nonlinear optical materials to have an absorption in the shorter wavelength range, and thus it means that the cutoff wavelength ($\lambda_{cut\ off}$) of below 390 nm in the nonlinear optical materials is suitable for the application.

The inorganic nonlinear optical materials currently in practical use as exemplified by lithium niobate and KTP have the disadvantage that they are very expensive and that their second order nonlinearity is not as high as that of organic materials. On the other hand, known organic nonlinear optical materials have the advantage that they are less costly and can be synthesized fairly easily. However, the absorption wavelength range of such organic materials, if they have a high SHG efficiency, extends to the visible region and their crystals show a yellow or orange color, which makes them useless to wavelength conversion of semiconductor lasers. In addition, it is usually difficult to grow large single crystals in many organic nonlinear optical materials.

Efforts have been made to shorten the absorption wavelength for several kind of organic nonlinear optical materials and they are exemplified by 3-methyl-4-nitropyridine-N-oxide (POM) and 4-hydroxy-3-methoxybenzaldehyde (Vanillin). However, FOM is insufficient for absorption cut off wavelengths, and Vanillin melts at a temperature as low as 83° C. with a lack of stability for the shinning light and in the air circumstance.

While practically feasible organic nonlinear optical materials should possess various characteristics, the following are particularly important:

1) high degree of optical nonlinearity;
2) high light transparency in the operating wavelength range, in particular, the range from 390 nm to 420 nm;
3) sufficiently high crystallinity to facilitate the production of large crystals;
4) high mechanical strength to assure ease in crystal processing; and
5) thermal and chemical stability.

None of the organic nonlinear optical materials known to date have been found to be promising since they do not satisfy all of these performance requirements.

SUMMARY OF THE INVENTION

Under the circumstances, it is an object of the present invention to provide an organic nonlinear optical material that exhibits a large nonlinear optical effect, that absorbs light in the shorter wavelength range, that has good crystallinity and processability, and which is sufficiently stable for use in practical applications.

It has now been found that the desired organic nonlinear optical material of improved quality can be provided by using the crystal of a compound selected from the group consisting of 4-chloro-4'-hydroxybenzophenone, methyl 3,4-diaminobenzoate, N-(4-aminobenzenesulfonyl)-acetamide, methyl 4-hydroxy-3,5-dimethoxybenzoate, 2-chloro-4-cyano-6-methylaniline, 4'-hydroxy-2-phenylacetophenone and methyl 3,4-dihydroxybenzoate.

DESCRIPTION OF THE PREFERRED EMBODIMENTS

In accordance with the present invention, there is provided an organic nonlinear optical material comprising the crystal of a compound selected from the group consisting of 4-chloro-4'-hydroxybenzophenone, methyl 3,4-diaminobenzoate, N-(4-aminobenzenesulfonyl)-acetamide, methyl 4-hydroxy-3,5-dimethoxybenzoate, 2-chloro-4-cyano-6-methylaniline, 4'-hydroxy-2-phenylacetophenone and methyl 3,4-dihydroxybenzoate.

The compounds used in the organic nonlinear optical material of the present invention are advantageous in the following points:

1) they exhibit a high degree of optical nonlinearity;
2) they absorb light at shorter wavelengths than the second harmonic light of a semiconductor laser used as a light source;
3) they have a very high degree of crystallinity;
4) they can produce hard crystals in a simple manner; and
5) they are stable with high melting points.

The crystals of these compounds can be formed by any of the known crystallization techniques in the art including solution growth (e.g., recrystallization), vapor-phase deposition and melt growth by selecting advantageous conditions as appropriate for the respective compounds. Details of crystallization techniques may be found in the book written by Shin-ichiro Takasu, "Kessho Ikusei Kiso Gijutsu (Basic Techniques for crystal growth)", 1980, which is incorporated herein by reference.

The hydrogen atom in the compounds to be used in the present invention may be deuterated to cause a bathochromic shift in the absorption of near infrared region, but as far as the nonlinear effect is concerned, no difference exists between deuterated and non-deuterated compounds. Therefore, part or all of the hydrogen atoms in the compounds listed above may be replaced by deuterium.

In a preferred embodiment of the present invention, the organic nonlinear optical material comprises the crystal of N-(4-aminobenzenesulfonyl)-acetamide.

The compounds specified by the present invention provide excellent organic nonlinear optical crystals and can effectively be used in second-order nonlinear optical devices (e.g., bulk wavelength conversion devices, slab waveguide wavelength conversion devices and crystal cored fiber wavelength conversion devices), optical waveguide devices and devices for upconversion of the frequency of light such as doubling of laser light.

The following examples are provided for the purpose of further illustrating the present invention but are in no way to be taken as limiting.

EXAMPLE 1

Commercially available 4-chloro-4'-hydroxybenzophenone (CHBP, product of Tokyo Kasei K.K., guaranteed reagent) was crystallized from acetone and ethanol in this order to yield a colorless and transparent plate-like crystal, which was found to have a melting point of 178° C. The visible and UV absorption spectra of the crystal were measured in a chloroform solution having a concentration of $10^{-5}$ mol per liter. The spectra showed a maximum absorption wavelength ($\lambda_{max}$) at 288.8 nm, with no absorption occurring at longer wavelengths beyond 400 nm. The melting point and maximum absorption wavelength of the crystal are shown in Table 1.

To evaluate the optical nonlinearity of the crystals, it was investigated by SHG measurement using the powder method, details of which are given in S. K. Kurtz and T. T. Perry, "A Powder Technique for the Evaluation of Nonlinear Optical Materials" in J. Appl. Phys., Vol. 39, pp. 3798–3813 (1966), which is also incorporated herein by reference.

The crystal as produced by recrystallization from ethanol was ground in a mortar and the powder was sieved to obtain fractions ranging from 63 to 100 microns in particle size. A dye laser (830 nm) excited by SHG from a Nd:YAG laser was used as a light source. A similarly prepared urea powder was used as a reference. The results are shown in Table 1, from which one can see that CHBP produced SHG which was 15 times as intense as the SHG of urea. Since CHBP is sufficiently transparent at the wavelength of second harmonic light of 830 nm, it is highly useful in wavelength conversion on semiconductor lasers.

EXAMPLES 2 TO 7

The procedure of Example 1 was repeated to recrystallize 2) methyl 3,4-diaminobenzoate, 3) N-(4-aminobenzenesulfonyl)-acetamide, 4) methyl 4-hydroxy-3,5-dimethoxybenzoate, 5) 2-chloro-4-cyano-6-methylaniline, 6) 4'-hydroxy-2-phenylacetophenone and 7) methyl 3,4-dihydroxybenzoate, which compounds were all available from Lancaster Corp.

The crystals obtained were measured for melting point, visible and UV absorption spectra and SHG by the same procedures as in Example 1, and the results are also shown in Table 1. As is apparent from Table 1, the compounds produced more intense SHG than urea.

Comparative Example

Commercially available 3-methyl-4-nitropyridine-N-oxide (POM, product of Tokyo Kasei K.K., guaranteed reagent) was recrystallized from acetone to yield a pale yellow three-dimensionally angular crystal, which was found to have a melting point of 136° C. The crystal was measured for visible and UV spectra and SHG by the same procedures as in Example 1. Maximum absorption occurred at the longest wavelength of all the compounds tested; in addition, visible light absorption extended to longer wavelengths beyond 415 nm, which is the second harmonic wavelength of 830 nm. The SHG from the comparative crystal was insufficient and only 0.97 times as intense as the SHG of urea. Therefore, the comparative crystal is not suitable for use in a device for wavelength conversion of semiconductor lasers.

TABLE 1

| Example | m.p. (°C.) | $\lambda_{max}$ (nm) | SHG intensity (at 830 nm against urea) |
| --- | --- | --- | --- |
| 1 | 178 | 288.8 | 15 |
| 2 | 109 | 310.4 | 6.3 |
| 3 | 184 | 267.0 | 6.4 |
| 4 | 107 | 273.8 | 2.8 |
| 5 | 132 | 271.6 | 5.5 |
| 6 | 151 | 274.0 | 1.1 |
| 7 | 135 | 293.2 | 4.4 |

TABLE 1-continued

| Example | m.p. (°C.) | $\lambda_{max}$ (nm) | SHG intensity (at 830 nm against urea) |
| --- | --- | --- | --- |
| Comparison | 136 | 338.6 | 0.97 |

What is claimed is:

1. An organic nonlinear optical material comprising the crystal of a compound selected from the group consisting of 4-chloro-4'-hydroxybenzophenone, methyl 3,4-diaminobenzoate, N-(4-aminobenzenesulfonyl)-acetamide, methyl 4-hydroxy-3,5-dimethoxybenzoate, 2-chloro-4-cyano-6-methylaniline, 4'-hydroxy-2-phenylacetophenone and methyl 3,4-dihydroxybenzoate.

2. An optical waveguide device comprising the organic nonlinear optical material claimed in claim 1.

3. A device for doubling the frequency of laser light comprising the organic nonlinear optical material claimed in claim 1.

* * * * *